(12) United States Patent  
Komatsu

(10) Patent No.: US 9,360,450 B2  
(45) Date of Patent: Jun. 7, 2016

(54) MEASURING DEVICE WITH ERROR CONTENT QUESTION SENTENCE AND USER-SELECTABLE CHOICES

(75) Inventor: Yuichiro Komatsu, Kyoto (JP)

(73) Assignee: HORIBA, LTD. (JP)

( * ) Notice: Subject to any disclaimer, the term of this patent is extended or adjusted under 35 U.S.C. 154(b) by 848 days.

(21) Appl. No.: 13/410,861

(22) Filed: Mar. 2, 2012

(65) Prior Publication Data

US 2012/0222467 A1 Sep. 6, 2012

(30) Foreign Application Priority Data

Mar. 3, 2011 (JP) ................................. 2011-046925

(51) Int. Cl.
  *G06F 3/0481* (2013.01)
  *G01N 27/416* (2006.01)
(52) U.S. Cl.
  CPC .................................. *G01N 27/4165* (2013.01)
(58) Field of Classification Search
  CPC ...................................................... G03G 15/55
  USPC .......................... 715/712, 709, 705, 710, 771
  See application file for complete search history.

(56) References Cited

U.S. PATENT DOCUMENTS

| | | | |
|---|---|---|---|
| 6,750,878 B1 | 6/2004 | Tatsuo et al. | |
| 8,808,178 B2 * | 8/2014 | Lane et al. | 600/300 |
| 2002/0097254 A1 * | 7/2002 | Simmons | 345/705 |
| 2009/0275805 A1 * | 11/2009 | Lane et al. | 600/300 |
| 2010/0219947 A1 * | 9/2010 | Kataoka | 340/461 |
| 2013/0318439 A1 * | 11/2013 | Landis et al. | 715/705 |

FOREIGN PATENT DOCUMENTS

| | | |
|---|---|---|
| JP | 63047879 A | 2/1988 |
| JP | 01121747 A | 5/1989 |
| JP | 02171657 A | 7/1990 |
| JP | 3191474 A | 8/1991 |
| JP | 11-038083 A | 2/1999 |
| JP | 2000155535 A | 6/2000 |
| JP | 2001016388 A | 1/2001 |
| JP | 2002083044 A | 3/2002 |
| JP | 2002160588 A | 6/2002 |
| JP | 2002171780 A | 6/2002 |
| JP | 2003079631 A | 3/2003 |
| JP | 2003203137 A | 7/2003 |

(Continued)

OTHER PUBLICATIONS

Extended European Search Report for Application No./Patent No. 12157855.3-2204, dated May 25, 2012, with English translation.

(Continued)

*Primary Examiner* — Namitha Pillai
(74) *Attorney, Agent, or Firm* — Cantor Colburn LLP

(57) ABSTRACT

The present invention is intended to make it possible to accurately and easily find out a solution when an error occurs and to make a display on a screen up to attaining the solution to be easily visible for a user, and has a solution display mode of sequentially displaying a plurality of question sentences in accordance with error content together with choices to the respective question sentences and displaying a next question sentence associated with the choice selected by a user and a choice to the next question sentence or a solution to the error content, and the choice to each of the question sentences is displayed together with a diagram showing the content of the corresponding choice.

4 Claims, 8 Drawing Sheets

(56) References Cited

FOREIGN PATENT DOCUMENTS

| | | |
|---|---|---|
| JP | 2004-163341 A | 6/2004 |
| JP | 2004163349 A | 6/2004 |
| JP | 2004-325077 A | 11/2004 |
| JP | 2006170868 A | 6/2006 |
| JP | 2007-327969 A | 12/2007 |
| JP | 2008-032493 A | 2/2008 |
| JP | 2009110432 A | 5/2009 |
| WO | 2009130852 A1 | 10/2009 |

OTHER PUBLICATIONS

Smart, Julian et al. "Cross-Platform GUI Programming with wxWidgets", 2006, Prentice Hall, Crawfordsville, USA, pp. 205-209.

Office Action for Japanese Patent Application No. 2011-046925, mailed Sep. 2, 2014, with English translation.

Japanese Decision to Grant Patent corresponding to Application No. 2011-046925; Date of Mailing: Mar. 19, 2015.

* cited by examiner

MEASURING DEVICE WITH ERROR CONTENT QUESTION SENTENCE AND USER-SELECTABLE CHOICES

TECHNICAL FIELD

The present invention relates to a measuring device capable of easily finding out a solution for an error when the error occurs.

BACKGROUND ART

Conventionally, as disclosed in Patent Literature 1, the present applicant considers a water quality measuring device in which a plurality of solutions are displayed in order to easily retrieve the solutions when an error occurs.

Specifically, in this water quality measuring device, if an error occurs, the occurrence of the error is displayed on a screen where a measurement value is indicated. Then, upon depression of a help key provided on an upper surface of the device body in this state, an outline of a plurality of solutions is displayed together with displaying, e.g., an error content of "calibration/incorrect potential error". Then, by selecting a solution which is likely to be appropriate as a solution for the error content among the plurality of solutions, a concrete solution is displayed.

CITATION LIST

Patent Literature

Patent Literature 1: JP2007-327969A

SUMMARY OF INVENTION

Technical Problem

However, in the water quality measuring device configured as mentioned above, there is a fear of selecting one solution among the plurality of solutions without knowing a cause of the error so as to be unable to select an effective solution, and therefore the present applicant newly paid attention to a problem of causing the need to try various solutions. Also, the present applicant paid attention to a problem that, although the plurality of solutions are displayed in outline, these solutions are poor in visibility for a user when displayed side by side so that there is also a fear of selecting an erroneous solution.

Therefore, an essential object of the present invention is to make it possible to accurately and easily find out a solution when an error occurs in a measuring device and to make a display on a screen up to reach a solution to be easily visible for a user.

Solution to Problem

That is, a measuring device according to the present invention includes a display control part displaying a measurement result obtained by measuring a measurement object on a display, wherein the display control part has a solution display mode of sequentially displaying a plurality of question sentences in accordance with error content together with choices to the respective question sentences on the display and displaying next question sentences associated with the choice selected by a user and a choice to the next question sentences or a solution to the error content, and wherein the choice to each of the question sentences is displayed together with a diagram showing the content of the corresponding choice.

With this configuration, it becomes possible for the user to reach the solution merely by selecting a relevant choice to each of the questions displayed on the display when an error occurs. Moreover, since a diagram showing the content of the choice is displayed in displaying the choice to each of the questions, the user can visually grasp the content of the choice so that the display on the screen up to reach the solution is easily visible for the user, and hence an erroneous selection of a choice is suppressed from causing.

Herein, in order to make the choices further more visible one by one so as to suppress an occurrence of an erroneous selection of a choice, it is preferable that the display control part displays a choice button as the choice on the display and that a choice sentence indicative of the content of the choice and a choice diagram indicative of the content of the choice are displayed within the choice button.

In addition, in order to make it possible for a user to visually grasp the content of not only the choices but also the solutions so as to improve the usability, it is preferable that the display control part displays an explanatory sentence indicative of the relevant solution and a diagram indicative of the content thereof at the time of displaying the solution.

According to a skill level of the user dealing with the measuring device, only a glance of an error content enables the user to remind the solution thereof. In this case, it is preferable that the display control part displays the relevant error content at the time of occurrence of the error and displays a selection screen for the user to select whether or not the mode is switched to the solution display mode. Thus, the measuring device can be made usable also for a skilled user.

Advantageous Effects of Invention

According to the present invention configured as described above, it becomes possible to accurately and easily find out a solution when an error occurs in the measuring device and to make the display on the screen up to reach a solution to be easily visible for a user.

DESCRIPTION OF EMBODIMENTS

The following describes one embodiment of the present invention with reference to the drawings.

A measuring device 100 according to the present embodiment is used for, e.g., surveys on water quality of such as rivers, lakes and oceans, managements of water quality in a nutrient solution or liquid cultivation, and a field measurement of wastewater from such as factories.

Figure 1:
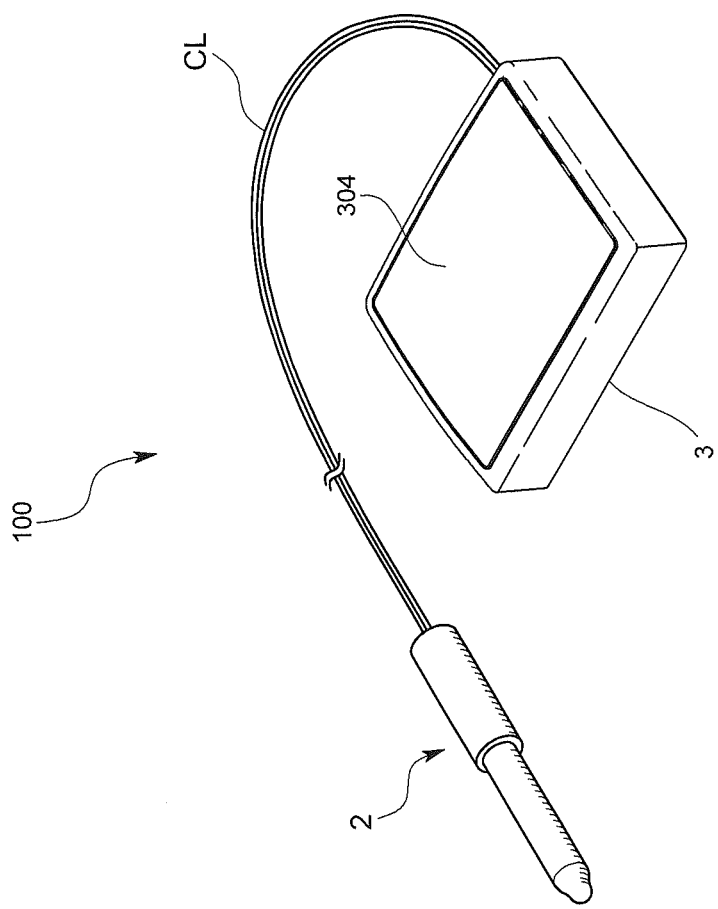
FIG. 1 is an overall schematic perspective view showing a measuring device in one embodiment of the present invention.

Specifically, as shown in FIG. 1, this measuring device includes a probe 2 to be brought into contact with a measurement object and a main body 3 connected to the probe 2 via wireless or a wired cable CL and measures a pH, oxidation/reduction potential, ion concentration, conductivity and dissolved oxygen so that the measured values thereof are displayed on a touch-panel type display 304 provided on the main body 3.

As the probe 2, a plurality of types, i.e., a pH measuring probe, an oxidation/reduction potential measuring probe, an ion concentration measuring probe, a conductivity measuring probe and a dissolved oxygen measuring probe, are prepared according to a measurement object so that the probe 2 appropriate for the measurement object is selectively connected to the main body 3 so as to be used. In the present embodiment, the following description is made using the pH measuring probe as a representative example of the probe 2.

The pH measuring probe 2 is a so-called composite electrode provided with a glass electrode and a reference electrode which are integrated with each other, wherein the glass electrode and reference electrode are exposed at a tip portion of the probe 2 so as to be brought into contact with a measurement object. The probe 2 in the present embodiment further includes an impedance conversion part inside a casing thereof so that a potential difference generated by the glass electrode and the reference electrode is impedance-converted and amplified by the impedance conversion part so as to be outputted as a probe output signal. It is noted that, although a standard type one is shown in FIG. 1, a needle type one having a sharp-pointed tip for use in sticking food and the like may be also used, and further it is needless to say that various types of the probe having such as a configuration of separately providing the glass electrode and the reference electrode may be also used.

Figure 2:
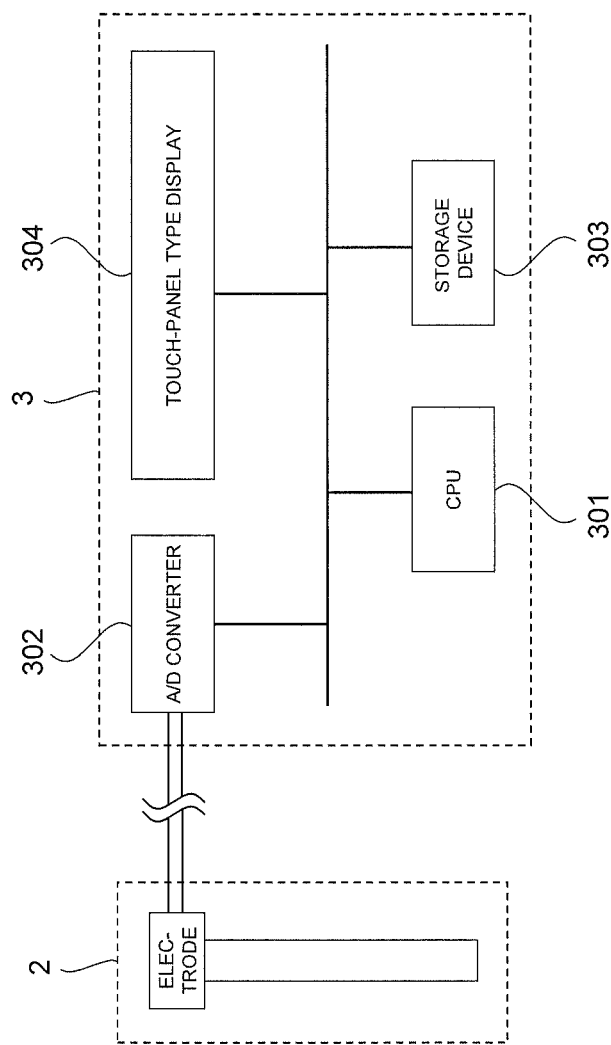
FIG. 2 is a hardware configuration diagram of the measuring device of the same embodiment.

As shown in FIGS. 1 and 2, the main body 3 is a dedicated one integrally provided with a CPU 301, an A/D converter 302, a storage device 303, a touch-panel type display 304 serving as both input means and display means and the like as a hardware configuration. Herein, the storage device 303 may include also a detachable non-volatile recording medium such as an externally connecting memory such as a compact flash memory and a USB memory in addition to an internal memory and the like. In addition, since the touch-panel type display 304 is used, the input means and the output means are integrated so that the main body 3 can be downsized.

Figure 3:
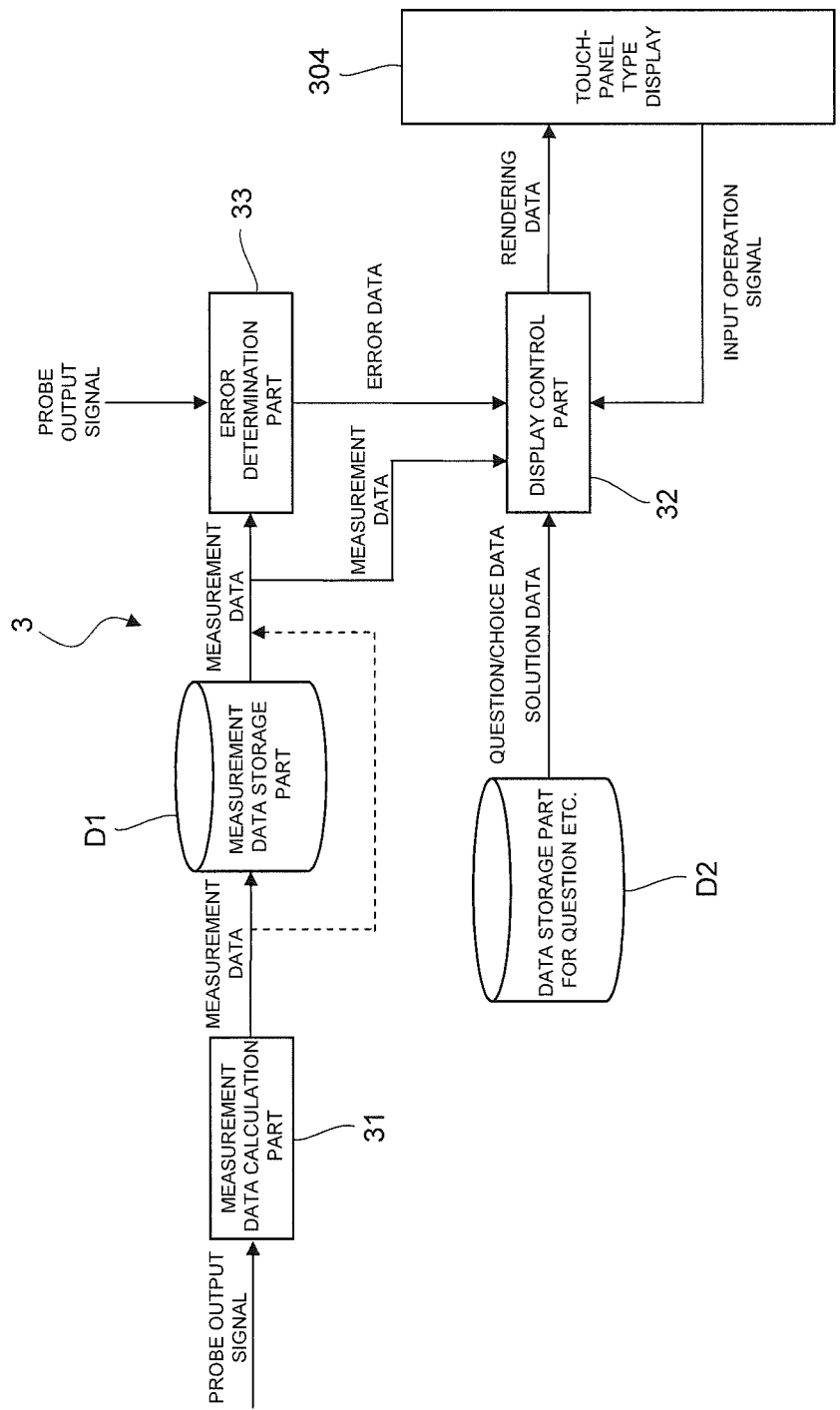
FIG. 3 is a functional block diagram of the measuring device of the same embodiment.

Thus, the CPU 301 and the peripherals thereof are operated based on programs stored in the storage device 303 so that the main body 3 functions as a measurement data calculation part 31, a measurement data storage part D1, a display control part 32, an error determination part 33, a data storage part D2 for a question etc. and the like, as shown in FIG. 3.

The measurement data calculation part 31 calculates measurement data indicative of a pH value (measurement value) of a measurement object from a value of the probe output signal sampled at predetermined intervals and sequentially converted to digital values by the A/D converter 302, i.e., based on a potential difference generated by the glass electrode and the reference electrode, through performing such as comparison between the above potential difference and a reference potential difference previously measured using a known buffer solution and stored in the storage device.

The measurement data storage part D1 is set to a predetermined region of the storage device 303 so as to sequentially store the measurement data sequentially calculated by the measurement data calculation part 31.

Figure 4:
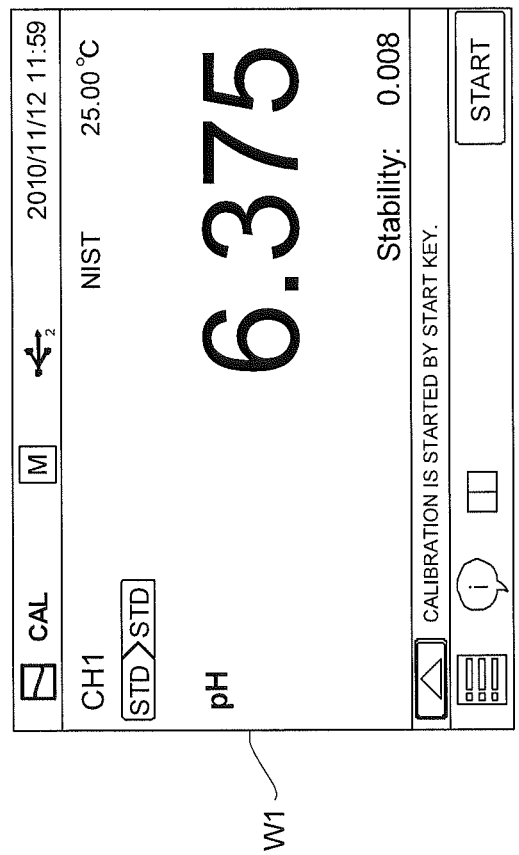
FIG. 4 is a screen display diagram showing a numerical display screen of the same embodiment.

The display control part 32 displays the value of the measurement data, i.e., pH value calculated by the measurement data calculation part 31 in various display formats on the touch-panel type display 304 in a measurement mode and a calibration mode. Specifically, as shown in FIG. 4, the display control part 32 displays a numerical value display screen W1 indicative of a numerical value of the pH on the display 304. Herein, FIG. 4 is a numerical value display screen in the calibration mode. In addition, the display control part 32 displays an analog display screen displaying a series of calibrated markings allocated with values at necessary positions and indication means indicating a position on the calibrated markings corresponding to the pH value, or displays a graph display screen displaying the pH value as a time series graph in a coordinate system in which one axis is a time axis indicating a time value and the other axis is a measurement axis indicating a pH value. These displays are switched to be displayed by a user's switching operation. Specifically, a user performs a touch-slide operation of the display 304 in a predetermined direction (right and left direction in the present embodiment) so that the display control part 32 acquires an input operation signal indicative of the corresponding touch-slide operation from the display 304 so as to switch to the respective display screens. In addition, the display control part 32 displays a switching button for switching various kinds of modes such as a measurement mode and a calibration mode, a measurement start button in the case of the measurement mode, a calibration start button in the case of the calibration mode, a help button for displaying a manual and a degree of stability of a pH value in the calibration mode, and the like on the display 304.

The error determination part 33 determines such as a measurement error in the measurement mode and a calibration error in the calibration mode. Specifically, the error determination part 33 compares the value of the probe output signal or the measurement data value calculated by the measurement data calculation part 31 with a predetermined error determination criterion so as to determine whether or not an error occurs. In the case where it is determined that an error occurs, the error determination part 33 outputs error determination data including the corresponding error content which is supplied to the display control part 32. Herein, there may be possibly a case of being out of measurement range, abnormality in electrode and abnormality in converter and the like as the measurement error in the measurement mode, and there may be possibly a case of abnormality in asymmetric potential, abnormality in sensitivity, abnormality in response speed, abnormality in standard solution and calibration interval error and the like as the calibration error in the calibration mode.

Figure 5:
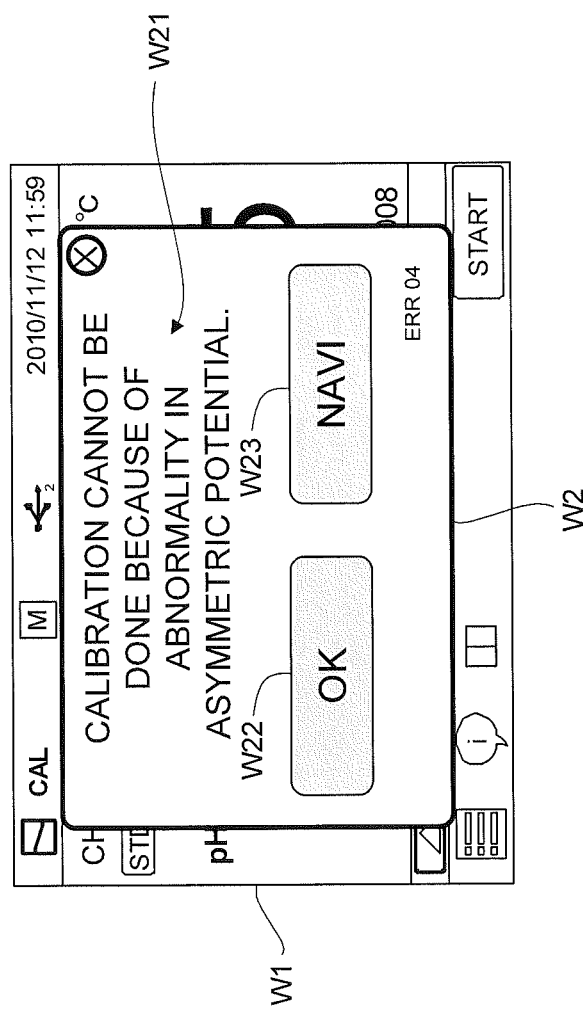
FIG. 5 is a screen display diagram showing a selection screen of the same embodiment.

Then, the display control part 32 after acquiring the error determination data from the error determination part 33 immediately displays a selection screen W2 superimposed on the corresponding numeric value display screen W1, separately from the numeric value display screen W1 on the display 304. In this selection screen W2, not only an error content W21 is displayed but also buttons W22 and W23 are displayed for a user to select whether or not the mode is switched to the solution display mode for solving the error content. Note that, in FIG. 5, there is shown an example of displaying a message that "Calibration cannot be done because of abnormality in asymmetric potential" in the case where abnormality in asymmetric potential occurs in the calibration mode. In addition, the button W22 displayed on the left is an OK button closing the selection screen W2 without shifting to the solution display mode. On the other hand, the button W23 displayed on the right is a NAVI button for shifting to the solution display mode. By providing the OK button W22 in this manner, a user who can remind the solution just by looking at the error content can save time and trouble in shifting to the solution display mode to find out the solutions one by one.

If the user selects the NAVI button W23 (screen-touch operation) in a state of displaying the selection screen W2, the display control part 32 shifts the mode to the solution display mode and displays the navigation screen W3 on the display 304 superimposed on the numeric value display screen W1 similarly to the selection screen W2. Then, the display control part 32 sequentially and hierarchically displays a plurality of question sentences together with choices for the respective question sentences on the navigation screen W3 according to the error content so as to display the solutions for the error content.

Herein, the question/choice data indicative of the question sentences and choices for the respective question sentences (also referred to as "question/choice" hereinafter) displayed on the navigation screen W3 and the solution data indicative of the solutions for the error content are previously stored in the data storage part D2 for a question etc. The multiple pieces of the question/solution data and solution data stored in the data storage part D2 for a question etc. are stored in association with every error determined by the error determination part 33. For example, the multiple pieces of question/choice data and solution data for every error are classified in a manner such as multiple pieces of question/choice data and solution data thereof corresponding to abnormality in asymmetric potential, multiple pieces of question/choice data and solution data thereof corresponding to abnormality in electrode and multiple pieces of question/choice data and solution data thereof corresponding to abnormality in standard solution so as to be stored. Further, the multiple pieces of question/choice data and solution data classified for the respective errors are hierarchically associated. Specifically, the question/solution data or the solution data displayed next for the respective choices are associated.

Then, the display control part 32 acquires, from the data storage part D2 for a question etc., the subsequent question sentences and choices for the subsequent question sentences or the solutions for the error content associated with the choices selected by the user so as to display them within the navigation screen W3.

Figure 6:
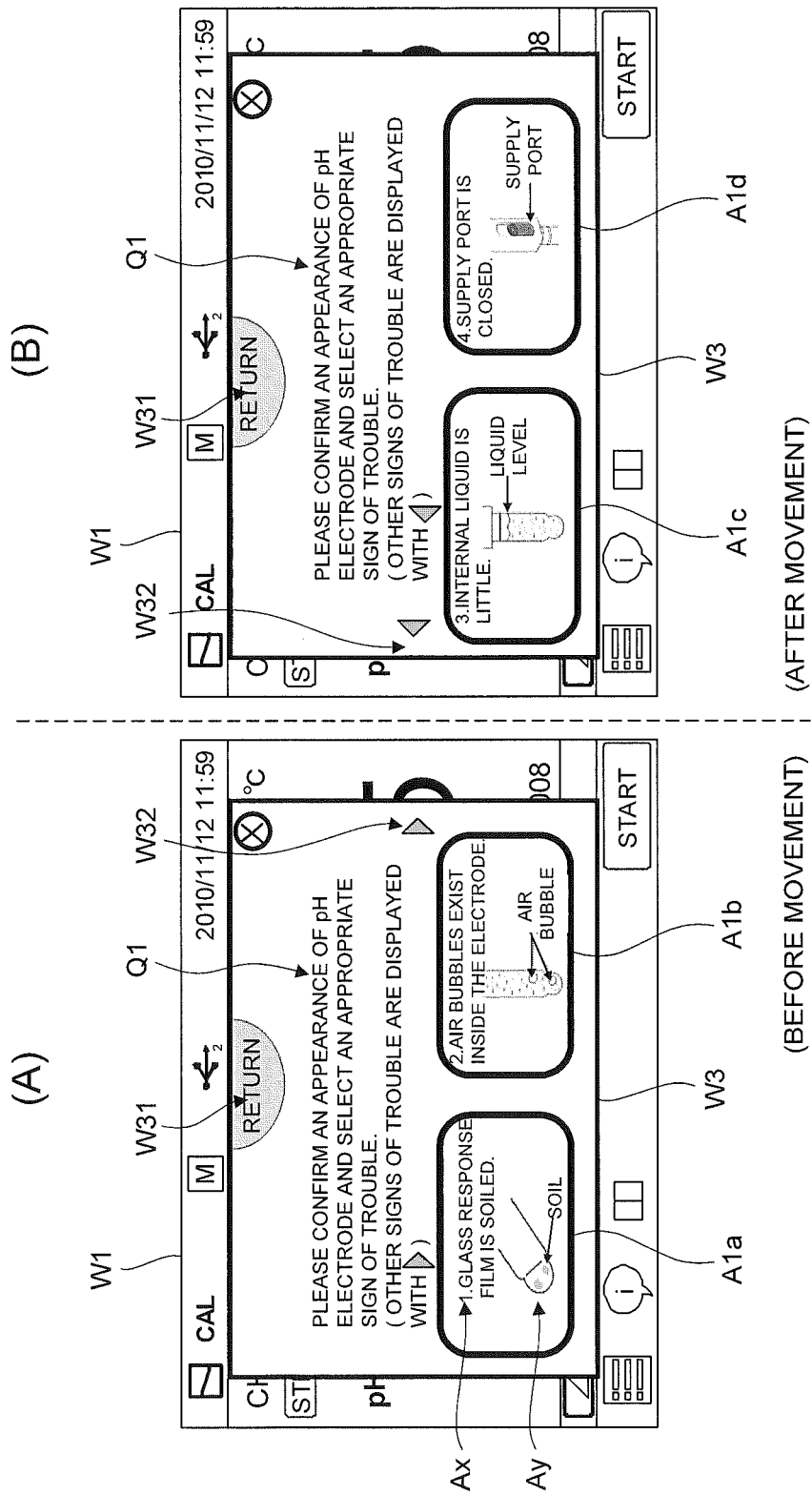
FIGS. 6(A) and (B) are screen display diagrams each showing a navigation screen of the same embodiment.

For example, in the abnormality in asymmetric potential, as shown in FIG. 6, there is displayed a question sentence Q1 of "Please confirm an appearance of a pH electrode and select an appropriate sign of trouble." as the first question sentence within the navigation screen W3. Also, a plurality of choice buttons A1a to A1d for the corresponding question sentence Q1 are displayed below the question sentence Q1. In the present embodiment, the two choice buttons A1a and A1b are displayed within the navigation screen W3 (see FIG. 6(A)), and regarding the choice buttons A1c and A1d which are not displayed within the navigation screen W3, the subsequent choice buttons A1c and A1d are displayed by touching a movement button W32 displayed at a predetermined position (rightmost end in the present embodiment) in the navigation screen W3. In addition, a return button W31 is provided within the navigation screen W3 so as to be able to return back to one-previous screen display (selection screen W2 or a screen displaying one-previous question/choice).

Herein, in the choice buttons A1a to A1d, a choice sentence Ax (including a case of only a word) appropriate as an answer to the question sentence Q1 and a choice diagram Ay indicative of the content of the corresponding choice sentence Ax are displayed. Note that the data indicative of the choice sentence and choice diagram is included in the question/choice data. As the choice diagram Ay, a schematic diagram indicative of the content of the choice sentence Ax and a title indicative of a characteristic part in the schematic diagram (a portion indicative of a main point of the choice or a concrete example) are displayed. In the present embodiment, although the choice sentence Ax is displayed in an upper portion and the choice diagram Ay is displayed in a lower portion within each of the choice buttons A1a to A1d, the positional relationship of the sentence Ax and diagram Ay is not particularly limited. In addition, the outline of each of the choice buttons A1a to A1d is frame-displayed with such as a thick line so as to be configured for a user to easily distinguish and visually identify each of the choices A1a to A1d.

Figure 7:
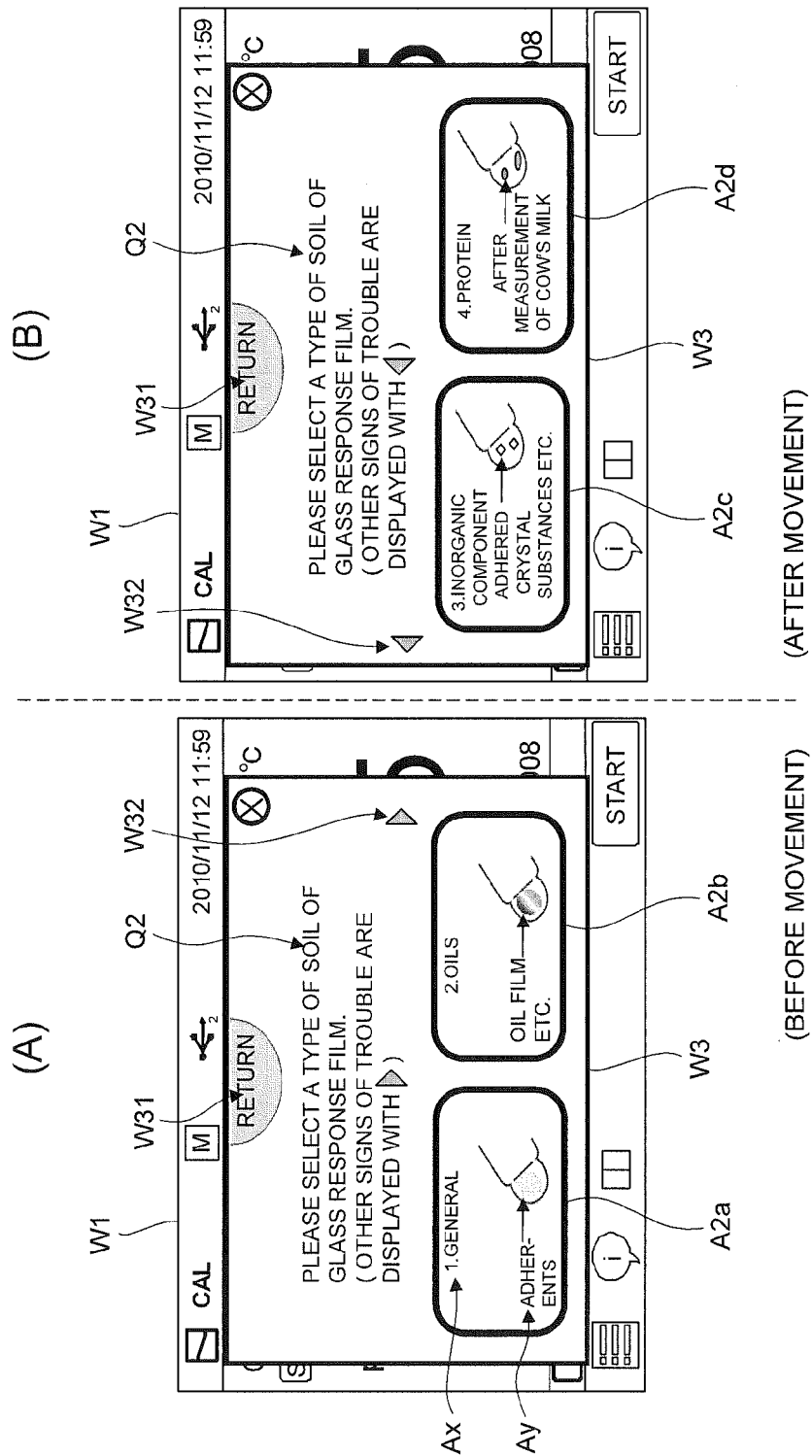
FIGS. 7(A) and (B) are screen display diagrams each showing a navigation screen of the same embodiment.

When one of the choice buttons A1a to A1d appropriate to the first question sentence Q1 is selected (by a screen-touch operation), the next question/choice in response to the corresponding one of the choices A1a to A1d is displayed. For example, in the abnormality in asymmetric potential, in the case where the choice button A1a ("glass response film is soiled") in FIG. 6 is selected, the display control part 32 acquires an input operation signal from the touch-panel type display 304 and determines that the choice button A1a is selected so as to acquire the next question/choice data corresponding to the choice button A1a from the data storage part D2 for a question etc. Specifically, as shown in FIG. 7, a question sentence Q2 of "Please select a type of soil of the glass response film" is displayed as the next question sentence within the navigation screen W3. Herein, the question sentence Q2 is the last question sentence in the abnormality in asymmetric potential. Further, a plurality of choice buttons A2a to A2d in response to the corresponding question sentence Q2 are displayed below the question sentence Q2. Moreover, similarly to the case of the question sentence Q1, two choice buttons A2a and A1b are being displayed within the navigation screen W3 (see FIG. 7(A)), and regarding the choice buttons A2c and A2d which are not displayed within the navigation screen W3, the next choice buttons A2c and A2d are displayed by performing a touch operation of the movement button W32 displayed at a predetermined position (rightmost end in the present embodiment) in the navigation screen W3.

Figure 8:
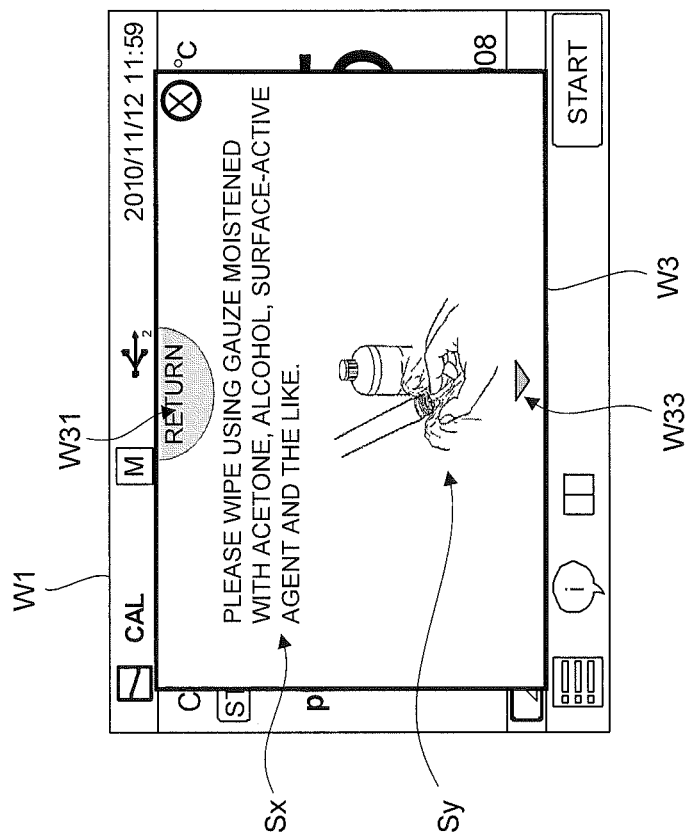
FIG. 8 is a screen display diagram showing a navigation screen of the same embodiment.

Then, if one of the choice buttons A2a to A2d appropriate to the last question sentence Q2 is selected (by a screen-touch operation), the solution for the error content associated with the corresponding choice is displayed. For example, in the abnormality in asymmetric potential, in the case where the choice button A2a ("General") in FIG. 7 is selected, the display control part 32 acquires an input operation signal from the touch-panel type display 304 and determines that the choice button A2a is selected so as to acquire the solution data associated with the corresponding choice button A2a from the data storage part D2 for a question etc. Then, the display control part 32 displays the content indicated by the corresponding solution data within the navigation screen W3. Specifically, as shown in FIG. 8, as a solution in the case where the soil of the glass response film is a general soil, an explanation sentence Sx that "Please wipe using gauze moistened with acetone, alcohol surface-active agent and the like" is displayed together with an explanatory diagram Sy indicative of the content thereof. In the present embodiment, although the explanation sentence Sx is displayed in the upper portion and the explanatory diagram Sy is displayed in the lower portion within the navigation screen W3, the positional relationship between the sentence Sx and the diagram Sy is not limited in particular. Herein, if there are multiple solutions, one of the solutions is displayed within the navigation screen W3 and the movement button W33 for displaying the other solutions is displayed.

In the above description, although a case of attaining a solution by providing the two questions Q1 and Q2 in the case of the abnormality in asymmetric potential, it is needless to say that a solution may be possibly attained by sequentially displaying three or more questions hierarchically in the case of the other error content.

According to the measuring device 100 according to the present embodiment configured as described above, when an error occurs, a user can attain a solution only by selecting (screen-touch operation) a relevant choice button for a question sentence displayed in the navigation screen W3 on the display 304. Moreover, since the choice sentence Ax and the choice diagram Ay indicative of the content thereof are displayed within the choice button for each question sentence, a user can visually grasp the content of the choice and the screen display up to attaining to the solution is easily visible for a user so as to suppress an occurrence of an erroneous selection of the choice. Moreover, since the touch-panel type display 304 is used in the present invention, a user can select a choice by a touch operation of the screen so that the usability of the measuring device 100 can be further improved.

It is noted that the present invention is not limited to the embodiments described above.

For example, in the present embodiment, although the touch-panel type display is used in consideration of user's usability, the input means having a group of buttons such as input buttons and the display may be separately provided in the main body.

Moreover, in the embodiment described above, although the choice buttons are displayed in sets of two within the navigation screen in order to facilitate visual identifications of the respective choice buttons and touch operations, three or more choice buttons may be displayed.

In addition, the present invention is not limited to the embodiments described above, and it is needless to say that various modifications may be made within a range without departing from the spirit of the invention.

REFERENCE SIGNS LIST

100 . . . Water quality measuring device (measuring device)
2 . . . Probe (measuring part)
3 . . . Main body
304 . . . Display
31 . . . Measurement data calculation part
32 . . . Display control part
33 . . . Error determination part
D1 . . . Measurement data storage part
D2 . . . Data storage part for question etc.

The invention claimed is:

1. A measuring device for use by a user to measure a measurement sample by using an electrode, the measuring device comprising:
   a main body comprising a display;
   a display control part structured to display on the display a measurement result obtained by measuring the measurement sample,
   wherein the display control part is structured to display at least one question sentence, in accordance with abnormality in the electrode, abnormality in asymmetric potential of the electrode, or abnormality in sensitivity of the electrode in a measurement or calibration, together with choices responsive to the respective question sentence on the display, each of the choices being indicative of a sign of trouble that causes the abnormality, and each of the choices being selectable by the user; and
   the display control part is structured to display at least one next question sentence associated with the choice selected by the user and a choice or choices responsive to the next question sentence or a solution to the abnormality, and
   wherein, for each choice to each of the question sentences, a choice sentence indicative of the sign of trouble that causes the abnormality, as well as a visual indicative of a characteristic part in an appearance of the electrode according to the sign of trouble in the choice sentence are displayed.

2. The measuring device according to claim 1, wherein the display control part displays a choice button as the choice on the display and the choice sentence and the visual are displayed within the choice button.

3. The measuring device according to claim 1, wherein the display control part displays the relevant error content at the time of occurrence of the abnormality in the electrode, abnormality in asymmetric potential of the electrode, or abnormality in sensitivity of the electrode and displays a selection screen for the user to select whether or not the mode is switched to the solution display mode.

4. The measuring device according to claim 1, wherein the display control part displays an explanatory sentence indicative of the relevant solution and a diagram indicative of the content thereof at the time of displaying the solution.

* * * * *